US005785642A

United States Patent [19]
Wallace et al.

[11] Patent Number: 5,785,642
[45] Date of Patent: Jul. 28, 1998

[54] METHODS FOR TREATING URINARY INCONTINENCE IN MAMMALS

[75] Inventors: George Wallace, Coto de Caza, Calif.; Richard J. Greff, St. Pete Beach, Fla.

[73] Assignee: Micro Therapeutics, Inc., San Clemente, Calif.

[21] Appl. No.: 734,016

[22] Filed: Oct. 18, 1996

[51] Int. Cl.$^6$ ........................................ A61F 2/02
[52] U.S. Cl. ............................ 600/30; 623/11; 424/423
[58] Field of Search .................. 623/11, 66; 600/29–30; 424/422–424, 430, 433

[56] References Cited

U.S. PATENT DOCUMENTS

| | | | |
|---|---|---|---|
| 4,631,188 | 12/1986 | Stoy et al. | 424/81 |
| 4,686,962 | 8/1987 | Haber | 128/DIG. 25 |
| 5,007,940 | 4/1991 | Berg | 600/30 |
| 5,336,263 | 8/1994 | Ersek et al. | |
| 5,580,568 | 12/1996 | Greft et al. | 424/423 |

OTHER PUBLICATIONS

Rodriguez, "Late Results of the Endourethral Infection of Teflon in Stress Urinary Incontinence," J. Urol. (Paris) 62: 39–41(1987).

Atala, et al., "Injectable Alginate Seeded with Chondrocytes as a Potential Treatment for Vesicoureteral Reflux," J. Urol., 150: 745–747 (1993).

Atala, et al., "Endoscopic Treatment of Vesicoureteral Reflux with a Self-Detachable Balloon System," J. Urol., 148: 724–727 (1992).

Capozza, et al., "Endoscopic Treatment of Vesico–Ureteric Reflux and Urinary Incontinence: Technical Problems in the Pediatric Patient," Br. J. Urol., 75: 538–542 (1995).

Kinugasa, et al., "Direct Thrombosis of Aneurysms with Cellulose Acetate Polymer", J. Neurosurg., 77:501–507 (1992).

Kinugasa, et al., "Early Treatment of Subarachnoid Hemorrhage After Preventing Rerupture of an Aneurysm", J. Neurosurg., 83:34–41 (1995).

Kinugasa, et al., "Prophylactic Thrombosis to Prevent New Bleeding and to Delay Aneurysm Surgery", Neurosurg., 36:661 (1995).

Lim, et al., "Periurethral Teflon Injection: A Simple Treatment for Urinary Incontinence," Br. J. Urol., 55: 208–210 (1983).

Malizia, et al., "Migration and Granulomatous Reaction After Periurethral Injection of Polytef (Teflon)," JAMA, 251(24): 3227–3281 (1984).

Moore, et al., "Periurethral Implantation of Glutaraldehyde Cross–Linked Collagen (Contigen ®) in Women with Type I or II Stress Incontinence: Quantitative Outcome Measures, "Br. J. Urol., 75: 359–363 (1995).

Merguerian, et al., "Submucosal Injection of Polyvinyl Alcohol Foam in Rabbit Bladder," J. Urol., 144: 531–533 (1990).

Murless, "The Injection Treatment of Stress Incontinence," J. Obstet. Gynaecol., 45: 67–73 (1938).

Park, et al., "New Polymers for Therapeutic Embolization", Poster #47, Meeting of Radiological Society of North America (1993).

Politano, et al., "Periurethral Teflon Injection for Urinary Incontinence," J. Urol., 111; 180–183 (1974).

Schulman, et al., "Endoscopic Injection of Teflon to Treat Urinary Incontinence in Women," BMJ, 288: 192–193 (1984).

Smart, "Poltef Paste for Urinary Incontinence," Aust. N. Z. J. Surg., 61: 663–666 (1991).

Stricker, et al., "Injectable Collagen for Type 3 Female Stress Incontinence: The First 50 Australian Patients," Med. J. Aust., 158: 89–91 (1993).

Taki, et al., "Selection and Combination of Various Endovascular Techniques in the Treatment of Giant Aneurysms", J. Neurosurg., 77:37–42 (1992).

Walker, et al., "Injectable Bioglass as a Potential Substitute for Injectable Polytetrafluoroethylene," J. Urol., 148: 645–647 (1992).

Winters, et al., "Periurethral Injection of Collagen in the Treatment of Intrinsic Sphincteric Deficiency in the Female Patient", Urologic Clinics of North America, 22(3):673–678 (1995).

Vesey, et al., "Teflon Injection in Female Stress Incontinence. Effect on Urethral Pressure Profile and Flow Rate," Br. J. Urol., 62: 39–41 (1988).

Primary Examiner—John P. Lacyk
Assistant Examiner—Rosiland Kearney
Attorney, Agent, or Firm—Burns, Doane, Swecker & Mathis, L.L.P.

[57] ABSTRACT

Disclosed are methods for treating urinary incontinence in a mammal wherein a composition comprising a biocompatible polymer, a biocompatible solvent, and a contrast agent is delivered to the periurethral tissue of the mammal.

13 Claims, No Drawings

METHODS FOR TREATING URINARY INCONTINENCE IN MAMMALS

BACKGROUND OF THE INVENTION

FIELD OF THE INVENTION

This invention is directed to methods for treating urinary incontinence in mammals generally and humans in particular. In these methods, a composition comprising a biocompatible polymer, a biocompatible solvent, and a contrast agent is delivered to the periurethral tissue of a mammal.

The biocompatible polymer is selected to be soluble in the biocompatible solvent, but insoluble in the periurethral tissue. The biocompatible solvent is miscible or soluble in the fluids of this tissue and, upon contact with such fluids, the biocompatible solvent quickly diffuses away whereupon the biocompatible polymer precipitates to form an occlusion in the periurethral tissue which compresses the urethra thereby preventing or reducing the involuntary leakage of urine from the bladder.

REFERENCES

The following publications are cited in this application as superscript numbers:

1 Murless, "The Injection Treatment of Stress Incontinence," *J. Obstet. Gynaecol.*, 45: 67–73 (1938).
2 Quackels, "Deux Incontinences Après Adénomecomie Guéries Par Injection de Paraffine Dans Le Périnée," Acta Urol. Belg., 23: 259–262 (1955).
3 Sachse, "Treatment of Urinary Incontinence with Sclerosing Solutions: Indications, Results, Complications," *Urol. Int.*, 15: 225–244 (1963).
4 Politano, et al., "Periurethral Teflon Injection for Urinary Incontinence," *J. Urol.*, 111: 180–183 (1974).
5 Lim, et al., "Periurethral Teflon Injection: A Simple Treatment for Urinary Incontinence," *Br. J. Urol.*, 55: 208–210 (1983).
6 Schulman, et al., "Endoscopic Injection of Teflon to Treat Urinary Incontinence in Women," *BMJ*, 228: 192 (1984).
7 Rodriguez, "Late Results of the Endourethral Injection of Teflon in Stress Urinary Incontinence," *J. Urol. (Paris)*, 62: 39–41 (1987).
8 Vesey, et al., "Teflon Injection in Female Stress Incontinence. Effect on Urethral Pressure Profile and Flow Rate," *Br. J. Urol.*, 62: 39–41 (1988).
9 Smart, "Poltef Paste for Urinary Incontinence," *Aust. N. Z. J. Surg.*, 61: 663–666 (1991).
10 Malizia, et al., "Migration and Granulomatous Reaction After Periurethral Injection of Polytef (Teflon)," *JAMA*, 251: 3227–3281 (1984).
11 Stricker, et al., "Injectable Collagen for Type 3 Female Stress Incontinence: The First 50 Australian Patients," *Med. J. Aust.*, 158: 89–91 (1993).
12 Moore, et al., "Periurethral Implantation of Glutaraldehyde CrossLinked Collagen (Contigen®) in Women with Type I or III Stress Incontinence: Quantitative Outcome Measures," *Br. J. Urol.*, 75: 359–363 (1995). 13 Capozza, et al., "Endoscopic Treatment of Vesico-Ureteric Reflux and Urinary Incontinence: Technical Problems in the Pediatric Patient," *Br. J. Urol.*, 75: 538–542 (1995).
14 Atala, et al., "Injectable Alginate Seeded with Chondrocytes as a Potential Treatment for Vesicoureteral Reflux," *J. Urol.*, 150: 745–747 (1993).
15 Meriguerian, et al., "Submucosal Injection of Polyvinyl Alcohol Foam in Rabbit Bladder," *J. Urol.*, 144: 531–533 (1990).
16 Walker, et al., "Injectable Bioglass as a Potential Substitute for Injectable Polytetrafluoroethylene," *J. Urol.*, 148: 645 (1992).
17 Atala, et al., "Endoscopic Treatment of Vesicoureteral Reflux with a Self-Detachable Balloon System," *J. Urol.*, 148: 724–728 (1992).
18 Kinugasa, et al., "Direct Thrombosis of Aneurysms with Cellulose Acetate Polymer", *J. Neurosurg.*, 77:501–507 (1992).
19 Kinugasa, et al., "Early Treatment of Subarachnoid Hemorrhage After Preventing Rerupture of an Aneurysm", *J. Neurosurg.*, 83:34–41 (1995).
20 Kinugasa, et al., "Prophylactic Thrombosis to Prevent New Bleeding and to Delay Aneurysm Surgery", *Neurosurg.*, 36:661 (1995). 21 Greff, et al., U.S. Pat. No. 5,580,568 for "Cellulose Diacetate Compositions for Use in Embolizing Blood Vessels", filed issued on Dec. 3, 1996.
22 Greff, et al., U.S. Pat. No. 5,667,767 for "Novel Compositions for Use in Embolizing Blood Vessels", issued on Sep. 16, 1997.
23 Taki, et al., "Selection and Combination of Various Endovascular Techniques in the Treatment of Giant Aneurysms", *J. Neurosurg.*, 77:37–42 (1992).
24 Park, et al., "New Polymers for Therapeutic Embolization", Poster #47, Meeting of Radiological Society of North America (1993)
25 Winters, et al., "Periurethral Injection of Collagen in the Treatment of Intrinsic Sphincteric Deficiency in the Female Patient", *Urologic Clinics of North America*,22 (3):473–478 (1995)

All of the above references are herein incorporated by reference in their entirety to the same extent as if each individual reference was specifically and individually indicated to be incorporated herein by reference in its entirety.
State of the Art Urinary incontinence is an extremely common problem especially in women. In particular, many women suffer from incontinence including stress incontinence. In this condition, the pelvic-floor muscles which support the base of the bladder and close off the top of the urethra are weakened by, for example, childbirth or obesity. As a result, when pressure is exerted on these muscles by coughing, lifting, etc., urine is involuntarily discharged from the bladder through the urethra.

The initial treatment for stress incontinence typically consists of exercises to strengthen the pelvic-floor muscles. If these exercises are ineffective, open surgical repair of the bladder neck is often attempted. However, such surgical repair procedures are not successful for all patients. Moreover, there are always certain risks associated with open surgical procedures, such as trauma, infection, risks of anesthesia, etc.

As an alternative to surgical repair, urinary incontinence has been treated by injecting various substances into the tissue surrounding the urethra, i.e., the periurethral tissue, to add bulk to this tissue. The aim of this treatment is to compress the urethra at the level of the bladder neck thus impeding the involuntary flow of urine from the bladder. Many substances have been tried for this purpose with varying results.

For example, Murless has reported the use of sodium morrhuate for the treatment of stress incontinence.[1] However, this material was not successful in preventing incontinence and pulmonary infarction was observed as a complication. Similarly, paraffin[2] and other sclerosing solutions[3] have been tried with poor results.

More recently, polytetrafluoroethylene particles (TEFLON™, POLYTEF™) have been used as an injectable material for the correction of urinary incontinence with a success rate of from 30% to 86% in some studies.[4-9] However, these particles have subsequently been demonstrated to generate foreign body granulomas and to migrate to distant organs, such as the lungs, liver, spleen and brain.[10] Accordingly, the use of polytetrafluoroethylene particles is currently disfavored.

Another injectable material that has been used recently for the treatment of urinary incontinence is glutaraldehyde cross-linked bovine dermal collagen.[11-13] However, a major problem associated with the use of collagen materials is the tendency of the implant to decrease in volume over time thereby necessitating retreatment.[14] In addition, collagen has been associated with adverse immune responses and allergic reactions to bovine dermal collagen have been described.[12]

Various other injectable substances have been reported or proposed as implant materials for the treatment of bladder conditions, such as vesicoureteral reflux. These substances include polyvinyl alcohol foam,[15] glass particles,[16] a chondrocyte-alginate suspension[14] and a detachable silicone balloon.[17]

In addition to the various problems associated with many of the substances used to treat urinary incontinence, the methods currently employed for delivering injectable materials to the periurethral tissue have certain disadvantages. In particular, the amount of material necessary to compress the urethra must typically be estimated by observing the compression of the urethra wall using a cystoscope or endoscope. If an insufficient amount of material is injected in the first procedure, top-up injections administered in subsequent procedures may be necessary.[11] Accordingly, it would be advantageous to be able to more accurately monitor the size of the occlusion formed by the injected material to ensure that it is sufficient to block the involuntary leakage of urine from the bladder. Additionally, if follow-up injections are necessary, it would be advantageous to be able to locate accurately the site of the material previously injected.

In view of the above, it is evident that there is an ongoing need in the art for new methods of treating urinary incontinence in mammals. Preferably, such methods would allow an occlusion-forming substance to be delivered accurately to the periurethral tissue. The substance employed would preferably conserve its volume in vivo, be non-migratory and be substantially non-immunogenic.

This invention is directed to the discovery that urinary incontinence can be treated in mammals by delivering sufficient amounts of a composition comprising a biocompatible polymer, a biocompatible solvent, and a contrast agent to the periurethral tissue under conditions such that a polymer precipitate forms in situ in the periurethral tissue. This polymer precipitate compresses the urethral opening thereby affording increased outlet resistance and reducing urinary incontinence in the mammal. The polymeric compositions of this invention are non-biodegradable and, accordingly, do not substantially decrease in volume over time. Moreover, the injection process provides for a coherent mass, not particulates, which mass is nonmigratory. Moreover, the contrast agent permits monitoring of the injection by conventional methods while it is taking place to ensure that it is being carried out properly. The contrast agent also allows monitoring post-injection by conventional methods to ensure correct placement of the mass months or even years after injection. Conventional monitoring methods include, by way of example, fluoroscopy, ultrasound, and in some cases visual detection.

SUMMARY OF THE INVENTION

This invention is directed to the discovery that unexpected and surprising results are achieved when mammals with urinary incontinence are treated with a composition comprising a biocompatible polymer, a biocompatible solvent, and a contrast agent. In particular, deficiencies associated with the prior art procedures are reduced by the invention. Such deficiencies include, for example, problems associated with migration of particulates over time, the biodegradation of the injected mass (e.g., collagen type materials) employed to form an occlusion in the periurethral tissue of the mammal, problems associated with the accurate delivery of such substances, and problems associated with post-delivery monitoring of the deposited materials.

Accordingly, in one of its method aspects, this invention is directed to a method for treating urinary incontinence in a mammal, which method comprises delivering a composition comprising a biocompatible polymer, a biocompatible solvent, and a contrast agent to the periurethral tissue of the mammal wherein said delivery is conducted under conditions such that a polymer precipitate forms in situ in the periurethral tissue thereby reducing the urinary incontinence in the mammal.

In another aspect of this invention, the use of a contrast agent is not required and the method is conducted by delivering a composition comprising a biocompatible polymer and a biocompatible solvent to the periurethral tissue of the mammal wherein said delivery is conducted under conditions such that a polymer precipitate forms in situ in the periurethral tissue thereby reducing the urinary incontinence in the mammal.

However, the use of a contrast agent in the composition is preferred.

The methods of this invention are preferably practiced using a kit of parts comprising:

a first member which is a polymeric composition comprising a biocompatible polymer, a biocompatible solvent and a contrast agent; and a second member which is a needle selected from the group selected of a puncture needle and spinal needle.

In the embolic compositions employed herein, the biocompatible polymer is preferably an ethylene vinyl alcohol copolymer or a cellulose acetate polymer. In a particularly preferred embodiment, the biocompatible polymer is selected to be substantially non-immunogenic.

The biocompatible solvent is preferably dimethylsulfoxide and, more preferably, anhydrous dimethylsulfoxide.

DETAILED DESCRIPTION OF THE INVENTION

This invention is directed to methods for treating urinary incontinence in mammals, which methods comprise delivering a composition comprising a biocompatible polymer, a biocompatible solvent, and a contrast agent to the periurethral tissue of the mammal.

Prior to discussing this invention in further detail, the following terms will first be defined:

The term "urinary incontinence" refers to the involuntary leakage of urine through the urethra from the bladder. Methods for diagnosing urinary incontinence are well known to those skilled in the relevant art. Such methods included, for example, video urodynamics and pad tests as described by Moore, et al.[12]

The term "periurethral tissue" refers to the tissue surrounding the urethra. As is understood in the art, the urethra is an orifice attached at its base to the bladder and permits discharge of urine from the bladder. Preferably, the polymeric compositions of the present invention are delivered to the periurethral tissue at or near the base of the urethra.

The term "biocompatible polymer" refers to polymers which, in the amounts employed, are non-toxic, non-peptidyl, non-migratory, chemically inert, and substantially non-immunogenic when used internally in the mammal and which are substantially insoluble in the periurethral tissue. The biocompatible polymers do not substantially decrease in volume over time and, since the polymer forms a solid inert mass, it does not migrate to distant organs within the body. Suitable biocompatible polymers include, by way of example, cellulose acetates[18-20] (including cellulose diacetate[21]), ethylene vinyl alcohol copolymers[22,23], polyalkyl($C_1$-$C_6$) acrylates, polyalkyl alkacrylates wherein the alkyl and the alk groups contain no more than 6 carbon atoms, polyacrylonitrile and the like. Additional biocompatible polymers are disclosed in U.S. patent application Ser. No. 08/655,822 entitled "Novel Compositions for Use in Embolizing Blood Vessels" which application is incorporated herein by reference in its entirety. Further examples of biocompatible polymers are provided by Park, et al.[24] Preferably, the biocompatible polymer is also non-inflammatory when employed in vivo.

The particular biocompatible polymer employed is not critical and is selected relative to the viscosity of the resulting polymer solution, the solubility of the biocompatible polymer in the biocompatible solvent, and the like. Such factors are well within the skill of the artisan.

Preferably, the biocompatible polymers do not appreciably absorb water upon contact with the fluid of the periurethral tissue and typically will have an equilibrium water content of less than about 25 % water and preferably less than about 15% water.

Particularly preferred biocompatible polymers include cellulose diacetate and ethylene vinyl alcohol copolymer. Cellulose diacetate polymers are either commercially available or can be prepared by art-recognized procedures. In a preferred embodiment, the number average molecular weight, as determined by gel permeation chromatography, of the cellulose diacetate composition is from about 25,000 to about 100,000; more preferably from about 50,000 to about 75,000; and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the occlusion-forming properties of the composition. Such additional monomers include, by way of example only, maleic anhydride, styrene, propylene, acrylic acid, vinyl acetate, and the like.

Ethylene vinyl alcohol copolymers are either commercially available or can be prepared by art-recognized procedures. Preferably, the ethylene vinyl alcohol copolymer composition is selected such that a solution of 6 weight percent of the ethylene vinyl alcohol copolymer, 35 weight percent of a tantalum contrast agent in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter or needle delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative solubility of the composition in the biocompatible solvent as well as the rate of precipitation of the copolymer in an aqueous solution (e.g., plasma). In a particularly preferred embodiment, the copolymers employed herein comprise a mole percent of ethylene of from about 25 to about 60 and a mole percent of vinyl alcohol of from about 40 to about 75. More preferably, these copolymers comprise from about 40 to about 60 mole percent of vinyl alcohol and from about 60 to 40 mole percent of ethylene. These compositions provide for requisite precipitation rates suitable for treating urinary incontinence in mammals.

The term "contrast agent" refers to a biocompatible (non-toxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a particle size of about 10 μm or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the periurethral tissue. Preferably, the biocompatible solvent is dimethylsulfoxide.

Compositions

The polymer employed in the methods of this invention are prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of the biocompatible polymer based on the total weight of the polymer composition, including contrast agent and biocompatible solvent, and more preferably from about 4 to about 5.2 weight percent. If necessary, gentle heating and stirring can be used to effect dissolution of the biocompatible polymer into the biocompatible solvent, e.g., 12 hours at 50° C.

Sufficient amounts of the contrast agent are then added to the solution to achieve the effective concentration for the complete polymer composition. Preferably, the polymer composition will comprise from about 10 to about 40 weight percent of the contrast agent and more preferably from about 20 to about 40 weight percent and even more preferably about 35 weight percent each based on the total weight of the polymer composition including the biocompatible polymer and the biocompatible solvent. When the contrast agent is not soluble in the biocompatible solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm). In one preferred embodiment, the particle size of a water insoluble contrast agent is prepared, for example, by fractionation. In such an embodiment, a water insoluble contrast agent such as tantalum having a particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under a microscope. The process is optionally repeated until a desired particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition may be heat sterilized and then stored preferably in sealed bottles (e.g., amber vials) or vials until needed.

Methods

The compositions described above are then employed in methods for treating urinary incontinence in mammals. In these methods, the composition is introduced to the periurethral tissue via conventional catheter or needle technology using, for example, cystoscopic techniques. Specifically, the injection may be performed through a puncture needle or spinal needle placed directly through the cystoscope or periurethrally with a spinal needle placed percutaneously at the introitus and positioned in the tissue adjacent to the urethra as described by Winters, et al.[25] Alternatively, the periurethral tissue can be exposed surgically and the composition injected directly into the tissue.

Upon discharge of the composition from the catheter or the needle into the periurethral tissue, the biocompatible solvent dissipates into the fluid of the periurethral tissue resulting in the precipitation of the biocompatible polymer which precipitate forms a coherent mass. The formed precipitate in the periurethral tissue swells this tissue restricting the urethral orifice thus impeding the involuntary flow of urine from the bladder.

The particular amount of polymer composition employed is dictated by the level of pre-existing support of the periurethral tissue, the concentration of polymer in the composition, the rate of precipitation (solids formation) of the polymer, etc. Such factors are well within the skill of the artisan. For example, individuals with weak pre-existing support of the periurethral tissue will require injection of more polymer composition in order to bulk up this tissue and constrict the urethra as compared to individuals with stronger pre-existing support.

The methods of this invention are particularly advantageous because the presence of the contrast agent in the composition permits, if desired, monitoring of the delivery of the biocompatible polymer while it is taking place either by fluoroscopy, ultrasound, or visually. In this way, one can ensure that the biocompatible polymer is being delivered to the optimal location in the periurethral tissue as well as determine whether the size of the polymer precipitate thus-formed will be sufficient to block the involuntary leakage of urine from the bladder.

Moreover, the treatment process can be modified by altering the rate of precipitation of the polymer which can be controlled merely by changing the overall hydrophobicity/hydrophilicity of the polymer. As is understood in the art, faster precipitation rates are achieved by a more hydrophobic polymer composition.

When delivery of the polymeric composition to the periurethral tissue is conducted via a cystoscope used in combination with a small diameter medical catheter (which typically employs a needle as described by Capozza, et al.[13]), the catheter employed is not critical provided that polymeric catheter components are compatible with the polymeric composition (i.e., the catheter components will not readily degrade in the polymer composition and none of the components of the polymer compositions will readily degrade in the presence of the catheter components). In this regard, it is preferred to use polyethylene in the catheter components because of its inertness in the presence of the polymeric composition described herein. Other materials compatible with the composition can be readily determined by the skilled artisan and include, for example, other polyolefins, fluoropolymers (e.g., polytetrafluoroethylene, perfluoroalkoxy resin, fluorinated ethylene propylene polymers), silicone, etc.

When introduced into the periurethral tissue, the biocompatible solvent rapidly diffuses into the fluids of this tissue leaving a solid precipitate. The precipitate is a coherent mass comprising a combination of the biocompatible polymer and the contrast agent. Without being limited to any theory, it is believed that this precipitate bulks up the periurethral tissue thereby increasing outlet resistance to urinary flow from the bladder. This enhanced outlet resistance reduces the urinary incontinence in the treated mammal.

Another advantage of this invention is that the precipitate forms a coherent mass which is substantially retained at the site of injection thereby obviating prior art concerns with migration of injected particulates into the periurethral tissue. Moreover, the polymeric compositions of this invention are non-biodegradable and, accordingly, do not substantially decrease in volume over time.

Still another advantage of this invention is that the polymer employed can be selected to be non-immunogenic thereby obviating concerns raised by use of collagen-type materials which can produce an immune response in vivo.

Yet another advantage of this invention is the formation of a polymeric mass in the periurethral tissue which mass contains a water insoluble contrast agent that permits the physician to monitor the implant over time to assure proper retention of the mass in the tissue. Additionally, if a subsequent injection is necessary to further reduce urinary incontinence in the mammal, placement of the additional polymeric material is facilitated when the material previously implanted can be visualized by, for example, fluoroscopy, ultrasound, and the like. A subsequent injection can occur at any time after the initial injection including, for example, months or years later.

In view of the above, the methods of this invention are preferably practiced using a kit of parts which kit contains a first member which is a polymeric composition comprising a biocompatible polymer, a biocompatible solvent and a contrast agent, and a second member which is a needle selected from the group consisting from a puncture needle and spinal needle.

Utility

The methods described herein are useful in treating mammals with urinary incontinence. Accordingly, these methods find use in human and other mammalian subjects requiring such treatment.

Additionally, it is contemplated that the compositions of this invention can be used to treat vesicoureteral reflux in a mammal. In this condition, urine from the bladder refluxes into a ureter often causing infection. It is contemplated the such reflux can be treated by delivering a composition comprising a biocompatible polymer, a biocompatible solvent, and a contrast agent to the subureteral tissue of the mammal. This delivery would be conducted under conditions such that a polymer precipitate forms in situ in the subureteral tissue thereby reducing vesicoureteral reflux in the mammal. The formation of a polymer precipitate in the subureteral tissue is expected to compress the ureter thereby reducing the reflux of urine into the ureter. Methods for delivering the composition to treat vesicoureteral reflux are described by Capozza, et al.[13]

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

cc= cubic centimeter

DMSO= dimethylsulfoxide

EVOH= ethylene vinyl alcohol copolymer mL= milliliter mm= millimeter

μm= micron

In the following examples, Examples 1-2 illustrate the preparation of polymer compositions useful in the methods described herein which polymer compositions comprise EVOH and cellulose acetate. Example 3 demonstrates the biocompatibility, non-migratory and bulking properties of an EVOH polymer in vivo.

Example 1

An EVOH polymer composition was prepared by combining 8 grams of EVOH (44 mole percent ethylene), 30 grams of tantalum having an average particle size of about 3 μm (narrow size distribution), and 100 mL of anhydrous DMSO. Heating at about 50° C. for about 12 hours was used to aid dissolution. The composition was mixed until homogeneous.

Tantalum having an average particle size of about 3 μm (narrow size distribution) was prepared by fractionation wherein tantalum, having an average particle size of less than about 20 μm, was added to ethanol (absolute) in a clean environment. Agitation of the resulting suspension was followed by settling for approximately 40 sec. to permit the larger particles to settle faster. Removal of the upper portion of the ethanol followed by separation of the liquid from the particles results in a reduction of the particle size which is confirmed under a microscope (Nikon Alphaphot™). The process was repeated, as necessary, until an average 3 μm particle size was reached.

Example 2

A cellulose diacetate polymer composition is prepared by combining 8 grams of cellulose acetate (39.7 weight percent acetyl content), 30 grams of tantalum having an aver age particle size of about 3 μm (narrow size distribution), and 100 mL of DMSO. The composition is mixed until homogeneous. Tantalum having an average particle size of about 3 μm (narrow size distribution) is prepared by fractionation as described in Example 1.

Example 3

The purpose of this example is to demonstrate the biocompatibility of an EVOH polymer with the bladder tissue of a mammal and to illustrate the non-migratory properties of such a polymer. Additionally, this example illustrates the ability of such a polymer to serve as a bulking agent in bladder tissue.

Female New Zealand white rabbits were utilized for this investigation. Using a 26 gauge needle, several 0.5 cc injections of an EVOH polymer composition, prepared in a manner essentially the same as that described in Example 1, were made submucosally in the bladder of each rabbit while the animals were under general anesthesia. Prior to sacrifice, x-rays were obtained to search for migration of the injected material. Two rabbits were sacrificed at one week post-injection and the bladders excised and examined histologically via 5 micron sectioning/staining of fresh-frozen and paraffin embedded tissue samples of the injection sites and surrounding areas. The injection sites showed black 5 pigmentation (tantalum) with some inflammation and cellular infiltration, i.e., a typical foreign body reaction. Tissues surrounding the injection site were normal. The implant had not migrated and appeared as one coherent mass.

From the foregoing description, various modifications and changes in the composition and method will occur to those skilled in the art. All such modifications coming within the scope of the appended claims are intended to be included therein.

What is claimed is:

1. A method for treating urinary incontinence in a mammal, which method comprises delivering a composition comprising a biocompatible polymer, a biocompatible solvent, and a contrast agent to the periurethral tissue of the mammal wherein said biocompatible polymer has an equilibrium water content of less than about 15% water and further wherein said delivery is conducted under conditions such that a coherent polymeric mass forms in situ in the periurethral tissue thereby reducing urinary incontinence in the mammal.

2. The method according to claim 1 wherein said biocompatible polymer is selected from the group consisting of cellulose acetate polymers, ethylene vinyl alcohol copolymers and polyacrylates.

3. The method according to claim 2 wherein said biocompatible polymer is a cellulose acetate polymer or an ethylene vinyl alcohol copolymer.

4. The method according to claim 1 wherein said biocompatible solvent is selected from the group consisting of dimethylsulfoxide, ethanol, and acetone.

5. The method according to claim 4 wherein said biocompatible solvent is dimethylsulfoxide.

6. The method according to claim 1 wherein said contrast agent is a water insoluble contrast agent.

7. The method according to claim 6 wherein said water insoluble contrast agent is selected from the group consisting of tantalum, tantalum oxide, tungsten, and barium sulfate.

8. The method according to claim 1 wherein said contrast agent is a water soluble contrast agent.

9. The method according to claim 8 wherein said water soluble contrast agent is metrizamide.

10. The method according to claim 1 wherein said composition is delivered into the periurethral tissue via a cystoscope.

11. A method for the delivery of a composition comprising a biocompatible polymer, a biocompatible solvent, and a water insoluble contrast agent to the periurethral tissue of the mammal which tissue already has deposited therein with an initial amount of this composition which method comprises visualizing the position of the deposited composition in the periurethral tissue delivering a composition comprising a biocompatible polymer, a biocompatible solvent, and a contrast agent to the periurethral tissue of the mammal containing said deposited composition wherein said biocompatible polymer has an equilibrium water content of less than about 15% water and further wherein said delivery is conducted under conditions such that additional coherent polymeric mass forms in situ in the periurethral tissue thereby further reducing urinary incontinence in the mammal.

12. The method according to claim 11 wherein visualization is conducted by direct visualization, fluoroscopy or ultrasound.

13. A method for treating urinary incontinence in a mammal, which method comprises delivering a composition comprising a biocompatible polymer and a biocompatible solvent to the periurethral tissue of the mammal wherein said biocompatible polymer has an equilibrium water content of less than about 15% water and further wherein said delivery is conducted under conditions such that a coherent polymeric mass forms in situ in the periurethral tissue thereby reducing urinary incontinence in the mammal.

* * * * *